(12) United States Patent
Pettit et al.

(10) Patent No.: US 6,281,196 B1
(45) Date of Patent: Aug. 28, 2001

(54) ISOLATION AND STRUCTURAL ELUCIDATION OF THE HUMAN CANCER CELL GROWTH INHIBITORY COMPOUND DENOMINATED AGELAGALASTATIN

(75) Inventors: George R. Pettit, Paradise Valley; Jun-Ping Xu, Chandler, both of AZ (US)

(73) Assignee: Arizona Board of Regents, Tempe, AZ (US)

( * ) Notice: Subject to any disclaimer, the term of this patent is extended or adjusted under 35 U.S.C. 154(b) by 0 days.

(21) Appl. No.: 09/719,082

(22) PCT Filed: Jun. 9, 1999

(86) PCT No.: PCT/US99/12935

§ 371 Date: Dec. 7, 2000

§ 102(e) Date: Dec. 7, 2000

(87) PCT Pub. No.: WO99/63942

PCT Pub. Date: Dec. 16, 1999

(51) Int. Cl.$^7$ ............................. A61K 38/00; A01N 43/04; C07H 15/00

(52) U.S. Cl. ............................. 514/25; 536/17.4; 31/70; 43/4

(58) Field of Search ............................. 514/25; 536/17.4

*Primary Examiner*—Dwayne C. Jones
(74) *Attorney, Agent, or Firm*—Richard R. Mybeck

(57) ABSTRACT

A human cancer cell line bioassay-directed investigation of the Western Pacific marine sponge agelas sp. led to isolation of a trace ($7.42 \times 10^{-6}$% yield) cancer cell growth inhibitor (lung NCI-H460 $GI_{50}$ 0.77 μg/ml to ovary OVCAR-3 $GI_{50}$ 2.8 μg/ml) designated agelagalastatin. Agelagalastatin is the first example of a natural product containing a digalactofuranosyl unit.

3 Claims, No Drawings

ISOLATION AND STRUCTURAL ELUCIDATION OF THE HUMAN CANCER CELL GROWTH INHIBITORY COMPOUND DENOMINATED AGELAGALASTATIN

This application is a 371 of PCT/US99/12935, filed on Jun. 9, 1999.

1. Field of the Invention

This invention relates generally to the field of chemotherapy and more particularly, to the discovery and structural elucidation of new cell growth inhibitor denominated "agelagalastatin" which was located in Western Pacific marine sponge Agelas sp.

This research was funded in part by the Outstanding Investigator Grant CA 44344-01A1-1922 and PHS Grant CA-16049-09-09-12, both awarded by the Division of Cancer Treatment, National Cancer Institute, DHHS. Accordingly, the United States government may have certain rights to this invention.

2. Background Art

Ancient marine invertebrate species of the *Phyla Bryozoa*, Molluska, and Porifera have been well established in the oceans for over one billion years. Such organisms have undergone trillions of biosynthetic reactions of their evolutionary chemistry to reach their present level of cellular organization, regulation and defense.

More particularly, marine sponges have changed minimally in their physical appearance over the last 500 million years. This suggests a very effective chemical resistance to evolution in response to changing environmental conditions over that period of time. Recognition of the potential for utilizing this biologically potent marine animal for medicinal purposes was recorded in Egypt about 2,700 B.C. and by 200 B.C. certain sea hare extracts were being used in Greece for their curative effect. This consideration along with the observation that marine animals, e.g., invertebrates and sharks, rarely develop cancer led to the systematic investigation of marine animal and plant anticancer compounds.

By 1968, ample evidence had been obtained, based on the U.S. National Cancer Institute's (NCI) key experimental cancer study systems, that certain marine organisms could provide new and antineoplastic and/or cytotoxic agents useful in chemotherapy and might also lead to compounds which would be effective in the control and/or eradication of viral diseases.

Further, these marine organisms were believed to possess potentially useful drug candidates of unprecedented structure which had eluded discovery by other methods of medicinal chemistry. Fortunately, these expectations have been realized, e.g. the discovery of the bryostatins, dolastatins and cephalostatins, and others, many of which are now in preclinical development or human clinical studies.

Those researchers who are presently involved in medicinal chemistry know well the time lag between the isolation of a new compound and its introduction to the market. Often this procedure takes several years and may take decades. As a result, industry, in association with the U.S. Government, has developed a system of testing criteria which serves two purposes. One is to eliminate those substances which are shown through testing to be economically counterproductive to pursue. The second, more important purpose serves to identify those compounds which demonstrate a high likelihood of success and therefore warrant the further study and qualification, and attendant expense, necessary to meet the stringent regulatory requirements which control the ultimate market place.

The current cost to develop the necessary data required for lawful marketing of a new drug compound approaches ten million dollars per compound. Economics dictate that such a huge investment be made only when there is a reasonable likelihood that it can be recovered. Absent such a likelihood, there will be no investment and, without investment, the research requisite for the discovery of these potentially life saving compounds will cease. Current research in the control of cancer in the United States is coordinated by the National Cancer Institute (NCI). To determine whether a substance has anti-cancer properties, the NCI has established a systematic protocol. This protocol, which involves the testing of a substance against a standard cell line panel containing 60 human tumor cell lines, has been verified and is accepted in scientific circles. The protocol, and the established statistical means for analyzing the results obtained by the standardized testing are fully described in the literature. See: Boyd, Dr. Michael R., *Principles & Practice of Oncology*, PPO Updates, Volume 3, Number 10, October 1989, for a general overview of the testing protocol; Monks, Anne et al., "Feasibility of a High-Flux Anticancer Drug Screen Using a Diverse Panel of Cultured Human Tumor Cell Lines", 83 *J. Nat. Cancer Inst.*, No. 11, 757 (1991); and Paull, K. D., "Display and Analysis of Patterns of Differential Activity of Drugs Against Human Tumor Cell Lines; Development of Mean Graph and COMPARE Algorithm", 81 *Journal of the National Cancer Institute Reports*, No. 14, 1088, (1989), for a description of the methods of statistical analysis. Each of these references are incorporated herein by this reference thereto.

Numerous substances have been discovered which demonstrate significant antineoplastic or tumor inhibiting characteristics. As stated above, many of these compounds have been extracted, albeit with great difficulty, from marine animals such as the sponge and sea hare. Once isolation and testing of these compounds has been accomplished, a practical question remains, namely, how to produce commercially significant quantities of the desired substance.

The work with substances extracted from living creatures has other problems not incurred with those substances sourced from botanicals. For example, quinine, which is available in practical quantities from the bark of the cinchona plant, differs materially from the compounds which are extracts of marine creatures possessing antineoplastic qualities. The collection and processing of these later compounds from their natural sources ranges from grossly impractical to the utterly impossible. Ignoring the ecological impact, the population of these creatures and the cost of collection and extraction make the process unworkable. Artificial synthesis of the active compounds is the only possible solution.

The isolation and identification of substances from living marine creatures requires that the structure of these antineoplastic compounds be elucidated. For only after the structure has been determined, can a means of synthesis be developed. This is often a long and arduous procedure because of the idiosyncratic complexity of these naturally occurring, evolutionary modified compounds. In addition, research is necessary to determine whether any portion of the naturally occurring compound is irrelevant to the desired properties, so that focus can be had on the simplest structure having the perceived properties.

DISCLOSURE OF INVENTION

In accordance with the overall program, a human cancer cell line bioassay-directed investigation of the Western Pacific marine sponge Agelas sp. led to isolation of a trace ($7.42 \times 10^{-6}$% yield) cancer cell growth inhibitor (lung NCI-H460 $GI_{50}$ 0.77 µg/ml to ovary OVCAR-3 $GI_{50}$ 2.8 µg/ml)

designated agelagalastatin (6). Agelagalastatin is the first example of a natural product containing a digalactofuranosyl unit.

The marine porifera genus Agelas (class Demospongae, order Agelasida, family Agelasidae) has previously been shown to be a rich source of new marine alkaloids (see D'Ambrosio et al., *Helv. Chim. Acta,* 1996, 79, 727.; Caffieri et al. (I), *Tetrahedron Lett.,* 1995, 36. 7893.; Jimenez et al., *Tetrahedron Lett.,* 1995, 35, 1375.) such as the cytotoxic (L1210 leukemia cell line) agelastatin A (1) (see: D'Ambrosio et al., *Helv. Chim. Acta,* 1996, 79, 727.) and a series of glycosphingolipids (Natori et el., *Tetrahedron,* 1994, 50, 2771.; Caffieri et al. (II), *Liebigs Ann. Chem.,* 1994, 1187.; Costantino et al. (I), *Liebigs Ann. Chem.,* 1994, 1181.; Costantino et al. (II), *Tetrahedron,* 1996, 52, 1573.; Caffieri et al. (III), *Liebigs Ann. Chem.,* 1995, 1477.; Costantino et al. (III), *Liebigs Ann. Chem.,* 1995, 1471; Morita et al., *J. Med. Chem.,* 1995, 38, 2176; Cafieri et al. (IV), *Gazz. Chim. Ita.,* 1996, 126, 711.) (cf 2 Natori et el., *Tetrahedron,* 1994, 50, 2771., 3 Caffieri et al. (II), *Liebigs Ann. Chem.,* 1994, 1187., 4 Costantino et al. (I), *Liebigs Ann. Chem.,* 1994, 1181., 5 Costantino et al. (II), *Tetrahedron,* 1996, 52, 1573). Some (e.g. 2 and 5) of these have shown immunomodulating activity, (see: D'Ambrosio et al., *Helv. Chim. Acta,* 1996, 79, 727.; Costantino et al. (II), *Tetrahedron,* 1996, 52, 1573) and a structural modification (5) (see: Morita et al., *J. Med. Chem.,* 1995, 38, 2176) has been considered for preclinical development as an anticancer (murine melanoma B16 in vivo active) and nonspecific immunostimulating agent. (See: D'Ambrsoio et al, *Helv. Chim. Acta,* 1996, 79, 727; Morita et al., *J. Med. Chem.,* 1995, 38, 2176.) Because glycosphingolipids (cerebrosides) are vitally important in a variety of biochemical processes ranging from antigenic specificity to cell-cell signaling and modulation of the immune response, discovery of new naturally occurring cancer cell growth inhibitory compounds is clearly necessary. The present disclosure is based upon our success in achieving the isolation and structural elucidation of the new glycosphingolipid agelagalastatin (6) from Agelas sp. which was collected off of the southeast coast of Papua New Guinea in the 1980's.

Accordingly, the primary object of the subject invention is the disclosure of the new in vitro cytostatic compound denominated "agelagalastatin".

Still another object of the present invention is the disclosure of the method of elucidation of the new in vitro cytostatic compound from marine sponge.

These and still further objects as shall hereinafter appear are readily fulfilled by the present invention in a remarkably unexpected manner as will be readily discerned from the following detailed description of exemplary embodiments thereof.

Statistical Definitions

The following measures are used to express drug activity by giving the drug dose which reduces cell growth to a specified percentage of growth:

$ED_{50}$ (P388) and $GI_{50}$ (HTCL) are the drug doses needed to reduce the percent growth to 50%. There is no mathematical difference between $ED_{50}$ and $GI_{50}$ which are both calculated using the same formula. The only difference is historical usage.

TGI, (Total Growth Inhibition), is the drug dose needed to yield zero percent growth, i.e., just as many cells at the end of the experiment as were present in the beginning. Whether just as many cells were killed as were produced (steady state), or no growth occurred (total inhibition), cannot be distinguished.

$LC_{50}$, (Lethal Concentration 50%), is the drug concentration which reduces growth to −50%, i.e., removes half of the cells originally present at the beginning of the experiment.

Each drug is tested at five (5) doses: 100–10–1–0.1–0.01 μg/ml. Percent Growths are calculated for each dose. The two (or three) doses with growth values above, below, (or near to) 50% growth are used to calculate the $ED_{50}/GI_{50}$ using a linear regression formula. The log of the dose is used during the regression computation. If no dose yields a growth value under 50%, the results are expressed as: $ED_{50}$ >(highest dose). If no dose yields growth higher than 50% growth, then $ED_{50}$ <(lowest dose). Similar calculations are performed for the TGI at 0% growth, and at −50% growth for the $LC_{50}$.

BEST MODE FOR CARRYING OUT THE INVENTION

Agelas sp. ( 450 kg wet wt.) was extracted with methanol and the alcohol-soluble portion was successively partitioned between 1:1 dichloromethane-methanol and water followed by n-hexane and 9:1 methanol-water and finally dichloromethane and 3:2 methanol-water. The resulting dichloromethane-soluble fraction (630.5 g) was separated (directed by human cancer cell line bioassays) by a series of gel permeation and partition chromatographic procedures on SEPHADEX LH-20 columns with the series methanol→n-hexane-dichloromethane-methanol (8:1:1)→n-hexane-isopropanol-methanol (8: 1:1)→n-hexane-toluene-acetone (1:4:4) as eluents to afford a fraction inhibitory to a selection of cancer cells. The bioactive fraction was treated with methanol to selectively isolate the more soluble active constituent herein named agelagalastatin (6, 6.5 mg, 7.42× $10^{-6}$% yield). The residual fraction was dissolved in dichloromethane-methanol (1:1) and subsequently identified (by NMR spectral analysis) as a mixture of monogalactosyl ceramides (See: Li et al., *Tetrahedron,* 1995, 51, 2273; Jin et al., *J. Org. Chem.,* 1994, 59, 144; Shin et al., *J. Nat. Prod.,* 1995, 58, 948; Mancini et al, *Helv. Chim. Acta,* 1994, 77, 51.) related to agelasphin-9b (2).

Agelagalastatin (6) was obtained as a colorless amorphous powder: $[\alpha]_D$+59° (c 0.65, $CH_3OH$) which showed a molecular ion peak in the HRFABMS spectrum at m/z 1192.7859 [M+Na]+ (calcd. 1192.7910) corresponding to molecular formula $C_{60}H_{115}NO_{20}$. When a 5.2 mg specimen of agelagalastatin was subjected to acid hydrolysis (15 h at 70°) with 1N HCl—$CH_3OH$ (8:91) followed by acetylation yielded methyl αβ-D-galactopyranoside tetracetate (identical with an authentic sample) and the sphiganine [(2S,3S,4R)-2-amino-15-methyl-1,3,4-hexadecanetriol and (2S,3S,4R)-2-amino-16-methyl-1,3,4-heptadecanetriol] were identified by physical and spectral data. The FABMS spectrum afforded three fragment ion peaks at m/z 1030.5 (M+Na+H-Gal)+, 868.5 (M+Na+H-2Gal)+, and 706.5 (M+Na+H-3Gal)+, suggesting the trisaccharide unit [Gal-Gal-Gal].

Interpretation of the $^1H$-$^1H$ COSY and TOCSY-NMR spectra led to assignment of the proton relay signals corresponding to five spin systems. The HMBC and ROESY 2D-NMR experiments supplied definitive structural information regarding connections to the five spin systems and allowed a view of the overall structure. Detailed data from HMQC and HMBC spectra suggested the ceramide unit was composed of two spin systems, namely 4-hydroxysphinganine and an α-hydroxy-ester. The latter was shown by mass spectral analysis of the preceding methanolysis products to be primarily a 2R-hydroxy-pentacosanoate with about 20% of the corresponding homologous 2R-hydroxy-tetracosanoate. Furthermore, the HMBC correlation peaks (Table 1) of C-1* with NH, H-2 and H-2* indicated that the two segments were linked together through an amide bond and all the chemical shifts shown by the ceramide units were reminiscent of those known for related compounds. (Natori et el., *Tetrahedron*, 1994, 50, 2771.; Caffieri et al. (II), *Liebigs Ann. Chem.*, 1994, 1187.; Costantino et al. (I), *Liebigs Ann. Chem.*, 1994, 1181.; Costantino et al. (II), *Tetrahedron*, 1996, 52, 1573.; Caffieri et al. (III), *Liebigs Ann. Chem.*, 1995, 1477.; Costantino et al. (III), *Liebigs Ann. Chem.*, 1995, 1471; Morita et al., *J. Med. Chem.*, 1995, 38, 2176; Cafieri et al. (IV), *Gazz. Chim. Ita.*, 1996, 126, 711).

The three anomeric proton signals appeared as doublets at δ5.47 (H-1'), 5.78 (H-1") and 5.61 (H-1'") and were a useful starting point for establishing the additional three spin systems. The heteronuclear chemical shift correlation (HMQC) spectrum was used to assign relationships between protons and carbon in the three carbohydrate units A, B, and C (Table 1). The $^{13}$C-NMR chemical shift data and the proton coupling constants measured by 2D-J resolution experiments revealed the inner galactose unit (A) to be a D-galactopyranoside. From consideration of the J value of the anomeric proton (H-1', J=4.0 Hz) as well as the chemical shift of the corresponding carbon (C-1',δ101.31), the anomeric aαconfiguration was assigned. The HMBC correlations of H-1/C-1' and H-1'/C-1 proved that the inner galactose segment (A) was directly connected with the C-1 ceramide hydroxyl by a glycosyl linkage.

Glycosylation shifts were observed at C-3' (+8.42 ppm) and C-2' (-2.36 ppm), along with HMBC correlations involving H-3'/C-1" and H-1" /C-3'. Both results signified that C-3' of galactose unit (A) was bonded through a glycoside link to the middle saccharide unit (B). The NOE correlation peaks of H-1/H-1' and H-3'/H-1" provided further evidence supporting two glycosyl linkages at two positions of the inner galactose section (A).

The two series of $^{13}$C chemical shifts displayed by units (B) and (C) were both characteristic of a D-galactofuranoside (Seo et al., *J. Am. Chem. Soc.*, 1978, 100, 3331). Because of the five-membered ring, the $^{13}$C chemical shifts of C-2", C-3", and C4" of unit (B) as well as those of C-2'", C-3'", and C-4'"of unit (C) (Table 1, shown below) were significantly downfield compared with the corresponding data for D-galactopyranoside. Additional NMR data (Table 1) suggested that the two furanoside units (B and C) corresponded to 1,4linked five-membered rings. Confirmatory evidence arose from the HMBC correlations of H-1"/C-4", H-1'"/C-4'" and H-4"/C-1'", which exactly defined the furanosyl 1,4-linkages, and from 2D-J resolution values attesting to the 2,3-diaxial (J=8.0 Hz) and 3,4-diaxial (J=8.0 Hz) relationships in the D-galactofuranoside (FIG. 1).

The chemical shifts of the anomeric carbons at δ 108.51 (C-1") and 101.69 (C-1'") together with the coupling constants of the anomeric protons (H-1", J=1.5 Hz and H-1'", J=4.5 Hz) allowed the middle (B) and outer D-galactofuranosyl units (C) to be assigned β- and α-configurations (George et al., *Can. J. Chem.*, 1975, 53, 1424), respectively. Furthermore, the NOE relationship from H-1" to H-3' together with HMBC correlation between H-1" and C-3' showed the presence of a 1"–3' glycosyl linkage between galactosyl sections A and B. The HMBC correlations of H-1'"/C-2" and H-2"/C-1'" combined with the NOE relationship of H-2"/H-1'" indicated that the outer furanose unit (C) was joined to the C-2" hydroxyl of the middle furanose (B). Thus, agelagalastatin was assigned structure 6 assuming that the overall stereochemistry and absolute configuration corresponds to that generally found for such glycosphingolipids. (Natori et el., *Tetrahedron*, 1994, 50, 2771.; Caffieri et al. (II), *Liebigs Ann. Chem.*, 1994, 1187.; Costantino et al. (I), *Liebigs Ann. Chem.*, 1994, 1181.; Costantino et al. (II), *Tetrahedron*, 1996, 52, 1573.; Caffieri et al. (III), *Liebigs Ann. Chem.*, 1995, 1477.; Costantino et al. (III), *Liebigs Ann. Chem.*, 1995, 1471; Morita et al., *J. Med. Chem.*, 1995, 38, 2176; Cafieri et al. (IV), *Gazz. Chim. Ita.*, 1996, 126, 711). To our knowledge, agelagalastatin (6) is the first marine animal constituent found to possess a digalactofuranosyl unit. Table 1. The High-Field (500 MHz) $^1$H- and $^{13}$C-NMR Spectral Data Found for Agelagalastatin (6)

| Position No. | $^{13}$C ppm | $^1$H ppm | J (Hz) | HMBC | Position No. | $^{13}$C ppm | $^1$H ppm | J (Hz) | HMBC |
|---|---|---|---|---|---|---|---|---|---|
| NH | | 8.58 d | 9.5 | 2, 1* | 1' | 101.31 d | 5.47 d | 4.0 | 1, 2', 3', 5' |
| 1 | 68.91 t | 4.42 m | 4.5, 12 | 2, 3, 1' | 2' | 68.54 d | 4.69 m | 4.0, 10 | 3' |
| | | 4.59 m | | | | | | | |
| 2 | 51.47 d | 5.24 m | 4.5, 9.0 9.5 | 1* | 3' | 80.02 d | 4.29 m | 5.0, 10 | 2', 5', 1" |
| 3 | 76.20 d | 4.29 m | 7.8, 9.0 | 1, 2, 5 | 4' | 70.41 d | 4.62 m | 5.0, 5.2 | 2', 3' |
| 4 | 72.80 d | 4.31 m | 7.8 | 6 | 5' | 72.43 d | 4.32 m | 4.0, 5.2 | 4', 6' |
| 5 | 34.05 t | 1.91 m | | | 6' | 62.76 t | 4.17 m | 4.0, 10.2 | |
| | | 2.26 m | | | | | 4.35 m | 4.0, 10.2 | |
| 6 | 26.47 t | 1.66 m | | | 1" | 108.51 d | 5.78 d | 1.5 | 3', 2", 4" |
| | | 1.91 m | | | | | | | |
| x | 39.26 t | 1.14 m | | z, z' | 2" | 88.74 d | 4.94 ddd | 1.5, 8.0 | 1", 1'" |
| y | 28.19 d | 1.44 m | | | 3" | 75.42 d | 4.94 m | 8.0, 8.0 | 2", 4" |
| z | 22.77 q | 0.86 d | | | 4" | 82.46 d | 4.74 dd | 3.8, 8.0 | 3" |
| z' | 22.77 q | 0.86 d | | x, y | 5" | 71.92 d | 4.36 m | 3.8, 7.0 | 6" |
| 1* | 175.31 s | | | | 6" | 64.47 t | 4.22 m | 7.0, 11 | 5" |
| | | | | | | | 4.16 m | 7.0, 11 | 5" |
| 2* | 72.50 d | 4.60 m | 4.2, 8.2 | 1*, 3*, 4* | 1'" | 101.69 d | 5.61 d | 4.5 | 2", 2'", 3'", 4'" |

-continued

| Position No. | $^{13}$C ppm | $^1$H ppm | J (Hz) | HMBC | Position No. | $^{13}$C ppm | $^1$H ppm | J (Hz) | HMBC |
|---|---|---|---|---|---|---|---|---|---|
| 3* | 35.60 t | 1.99 m<br>2.20 m | | | 2''' | 79.07 d | 4.57 dd | 4.5, 8.0 | 3''' |
| 4* | 25.87 t | 1.66 m<br>1.74 m | | | 3''' | 75.18 d | 5.14 t | 8.0, 8.0 | 2''', 4''', 5''' |
| x* | 32.11 t | 1.22 m | | | 4''' | 83.26 d | 4.55 dd | 3.5, 8.0 | 1''', 3''', 5''' |
| y* | 22.92 t | 1.24 m | | z* | 5''' | 72.83 d | 4.43 m | 3.5, 7.0 | |
| z* | 14.26 q | 0.85 t | | x*, y* | 6''' | 64.43 t | 4.23 m<br>4.30 m | 7.0, 11<br>7.0, 11 | 4'''<br>4''' |

1) x, y, z and x*, y*, z* represent the third, second and first positions from the terminal of the long chains, respectively.
2) Each coupling constant (J value) of the protons was confirmed with analysis of 2D-J resolution spectrum.

Agelagalastatin (6) displayed significant in vitro activity against a portion of our minipanel (including brain SF-295, renal A498, colon KM20L2 and melanoma SK-MEL-5) of human cancer cell lines with $GI_{50}$ values ranging from 0.77 µg/ml for lung NCI-H460 to 2.8 µg/ml for the ovarian OVCAR-3. Additional research, based on our discovery of agelagalastatin, will entail confirmation of the stereochemistry by total synthesis followed by detailed biological evaluation.

The dosage administered will be dependent upon the identity of the neoplastic disease; the type of host involved, including its age, health and weight; the kind of concurrent treatment, if any; the frequency of treatment and therapeutic ratio.

Illustratively, dosage levels of the administered active ingredients are: intravenous, 0.1 to about 20 mg/kg; intramuscular, 1 to about 50 mg/kg; orally, 5 to about 100 mg/kg; intranasal instillation, 5 to about 100 mg/kg; and aerosol, 5 to about 100 mg/kg of host body weight.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions of suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously, the tablet can be provided with a protective coating consisting of a sealing coat or enteric coat of shellac, a coating of sugar and methylcellulose and polish coating of carnauba wax.

Fluid unit dosage forms for oral administration such as in syrups, elixirs and suspensions can be prepared wherein each teaspoonful of composition contains a predetermined amount of an active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably P.F. water, a dry powder can be formulated when insufflation is the administration of choice.

For use as aerosols, the active ingredients can be packaged in a pressurized aerosol container together with a gaseous or liquified propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof. Several dosage forms were prepared embodying the present invention. They are shown in the following examples in which the notation "active ingredient" signifies agelagalastatin or any other compound. described herein.

COMPOSITION "A"

Hard-Gelatin Capsules

One thousand two-piece hard gelatin capsules for oral use, each capsule containing 20 mg of an active ingredient are prepared from the following types and amounts of ingredients:

| Active ingredient, micronized | 20 g |
|---|---|
| Corn Starch | 20 g |
| Talc | 20 g |
| Magnesium stearate | 2 g |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing an active ingredient in 5, 25 and 50 mg amounts by substituting 5 g, 25 g and 50 g of an active ingredient for the 20 g used above.

COMPOSITION "B"

Soft Gelatin Capsules

One-piece soft gelatin capsules for oral use, each containing 20 mg of an active ingredient, finely divided by means of an air micronizer, are prepared by first suspending the compound in 0.5 ml of corn oil to render the material capsulatable and then encapsulating in the above manner.

The foregoing capsules are useful for treating a neoplastic disease by the oral administration of one or two capsules one to four times a day.

COMPOSITION "C"

Tablets

One thousand tablets, each containing 20 mg of an active ingredient, are prepared from the following types and amounts of ingredients:

| Active ingredient, micronized | 20 g |
|---|---|
| Lactose | 300 g |
| Corn starch | 50 g |
| Magnesium stearate | 4 g |
| Light liquid petrolatum | 5 g |

The active ingredient, finely divided by means of an air micronizer, is added to the other ingredients and then thoroughly mixed and slugged. The slugs are broken down by forcing them through a Number Sixteen screen. The resulting granules are then compressed into tablets, each tablet containing 20 mg of the active ingredient.

The foregoing tablets are useful for treating a neoplastic disease by the oral administration of one or two tablets one to four times a day.

Using the procedure above, tablets are similarly prepared containing an active ingredient in 25 mg and 10 mg amounts by substituting 25 g and 10 g of an active ingredient for the 20 g used above.

COMPOSITION "D"

Oral Suspension

One liter of an aqueous suspension for oral use, containing in each teaspoonful (5 ml) dose, 5 mg of an active ingredient, is prepared from the following types and amounts of ingredients:

| Active ingredient, micronized | 1 g |
|---|---|
| Citric acid | 2 g |
| Benzoic acid | 1 g |
| Sucrose | 790 g |
| Tragacanth | 5 g |
| Lemon Oil | 2 g |
| Deionized water, q.s. | 1000 ml |

The citric acid, benzoic acid, sucrose, tragacanth and lemon oil are dispersed in sufficient water to make 850 ml of suspension. The active ingredient, finely divided by means of an air micronizer, is stirred into the syrup unit uniformly distributed. Sufficient water is added to make 1000 ml.

The composition so prepared is useful for treating a neoplastic disease at a dose of 1 teaspoonful (15 ml) three times a day.

COMPOSITION "E"

Parenteral Product

A sterile aqueous suspension for parenteral injection, containing 3 mg of an active ingredient in each milliliter for treating a neoplastic disease, is prepared from the following types and amounts of ingredients:

| | |
|---|---:|
| Active ingredient, micronized | 3 g |
| POLYSORBATE 80 | 5 g |
| Methylparaben | 2.5 g |
| Propylparaben | 0.17 g |
| Water for injection, q.s. | 1000 ml. |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1 ml) three times a day.

COMPOSITION "F"

Suppository, Rectal and Vaginal

One thousand suppositories, each weighing 2.5 g and containing 20 mg of an active ingredient are prepared from the following types and amounts of ingredients:

| | |
|---|---:|
| Active ingredient, micronized | 1.5 g |
| Propylene glycol | 150 g |
| Polyethylene glycol #4000, q.s. | 2,500 g |

The active ingredient is finely divided by means of an air micronizer and added to the propylene glycol and the mixture passed through a colloid mill until uniformly dispersed. The polyethylene glycol is melted and the propylene glycol dispersion is added slowly with stirring. The suspension is poured into unchilled molds at 40° C. The composition is allowed to cool and solidify and then removed from the mold and each suppository foil wrapped.

The foregoing suppositories are inserted rectally or vaginally for treating a neoplastic disease.

COMPOSITION "G"

Intranasal Suspension

One liter of a sterile aqueous suspension for intranasal instillation, containing 20 mg of an active ingredient in each milliliter, is prepared from the following types and amounts of ingredients:

| | |
|---|---:|
| Active ingredient, micronized | 1.5 g |
| POLYSORBATE 80 | 5 g |
| Methylparaben | 2.5 g |
| Propylparaben | 0.17 g |
| Deionized water, q.s. | 1000 ml. |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease, by intranasal instillation of 0.2 to 0.5 ml given one to four times per day.

An active ingredient can also be present in the undiluted pure form for use locally about the cutis, intranasally, pharyngolaryngeally, bronchially, or orally.

COMPOSITION "H"

Powder

Five grams of an active ingredient in bulk form is finely divided by means of an air micronizer. The micronized powder is placed in a shaker-type container.

The foregoing composition is useful for treating a neoplastic disease, at localized sites by applying a powder one to four times per day.

COMPOSITION "I"

Oral Powder

One hundred grams of an active ingredient in bulk form is finely divided by means of an air micronizer. The micronized powder is divided into individual doses of 20 mg and packaged.

The foregoing powders are useful for treating a neoplastic disease, by the oral administration of one or two powders suspended in a glass of water, one to four times per day.

COMPOSITION "J"

Insufflation

One hundred grams of an active ingredient in bulk form is finely divided by means of an air micronizer.

The foregoing composition is useful for treating a neoplastic disease, by the inhalation of 300 mg one to four times a day.

From the foregoing, it becomes readily apparent that a new and useful antineoplastic factor and new and useful antineoplastic preparations have been herein described and illustrated which fulfill all of the aforestated objectives in a remarkably unexpected fashion. It is of course understood that such modifications, alterations and adaptations as will readily occur to the artisan confronted with this disclosure are intended within the spirit of the present invention.

What is claimed is:

1. A cytostatic compound denominated "agelagalastatin" having the following structure:

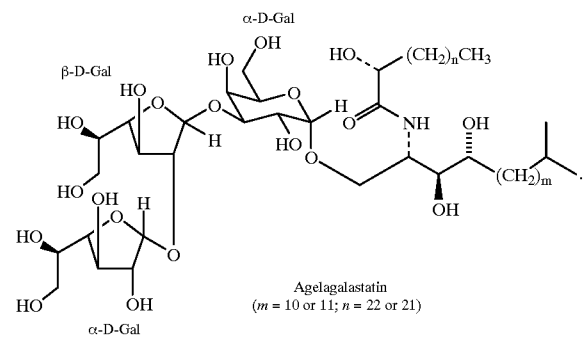

Agelagalastatin
($m$ = 10 or 11; $n$ = 22 or 21)

2. The method of treating cells afflicted with neoplastic disease selected from the group consisting of brain, renal, colon cancers and melanoma comprising engaging said cells with an effective amount of agelagalastatin disposed in a pharmacologically acceptable carrier.

3. A pharmaceutical preparation for treating neoplastic disease comprising an effective amount of agelagalastatin and a pharmaceutically acceptable carrier.

* * * * *